United States Patent
Wallauer

(10) Patent No.: US 8,598,869 B2
(45) Date of Patent: Dec. 3, 2013

(54) MAGNETIC FIELD COMPENSATION

(75) Inventor: Steffen Wallauer, Roxheim (DE)

(73) Assignee: Integrated Dynamics Engineering GmbH, Raunheim (DE)

( * ) Notice: Subject to any disclaimer, the term of this patent is extended or adjusted under 35 U.S.C. 154(b) by 574 days.

(21) Appl. No.: 12/792,862

(22) Filed: Jun. 3, 2010

(65) Prior Publication Data

US 2010/0308811 A1    Dec. 9, 2010

(30) Foreign Application Priority Data

Jun. 5, 2009   (DE) .................. 10 2009 024 268

(51) Int. Cl.
   *G01N 27/72*   (2006.01)
   *G01N 27/90*   (2006.01)

(52) U.S. Cl.
   CPC ................ *G01N 27/9053* (2013.01)
   USPC ........................................ 324/225

(58) Field of Classification Search
   None
   See application file for complete search history.

(56) References Cited

U.S. PATENT DOCUMENTS

| | | |
|---|---|---|
| 3,801,877 A | 4/1974 | Griese et al. |
| 4,198,021 A | 4/1980 | Meredith et al. |
| 5,225,999 A | 7/1993 | Luzzi |
| 5,465,012 A | 11/1995 | Dunnam |
| 5,519,318 A | 5/1996 | Koerner et al. |
| 5,586,064 A | 12/1996 | Grupp |
| 6,124,712 A | 9/2000 | Chaiken |
| 7,715,948 B2 * | 5/2010 | Heiland .................. 700/280 |
| 7,859,259 B2 * | 12/2010 | Heiland .................. 324/253 |
| 2001/0052431 A1 | 12/2001 | Klauer et al. |
| 2005/0099177 A1 | 5/2005 | Greelish |
| 2007/0233325 A1 | 10/2007 | Heiland |
| 2008/0012559 A1 | 1/2008 | Heiland |
| 2009/0184706 A1 * | 7/2009 | Duric et al. ............. 324/202 |

FOREIGN PATENT DOCUMENTS

| | | |
|---|---|---|
| DE | 33 08 717 A1 | 9/1984 |
| DE | 197 18 649 A1 | 11/1998 |
| EP | 1 840 681 A1 | 10/2007 |
| EP | 1 860 451 A1 | 11/2007 |
| EP | 1 873 543 A1 | 1/2008 |
| JP | 2002022528 A | 1/2002 |
| JP | 2005-069829 | 3/2005 |
| JP | 2005069829 A | 3/2005 |
| JP | 2005283191 A | 10/2005 |
| JP | 2007265414 A | 10/2007 |
| JP | 2008014944 A | 1/2008 |
| WO | 2007138508 A1 | 12/2007 |

OTHER PUBLICATIONS

Böhm-Pelissier, A. "International Search Report for parallel European Patent Application No. EP 10 00 5738", Oct. 18, 2010, Publisher: European Patent Office.
Dipl.-Ing. Abeln, "German Office Action for International Application No. 10 2009 024 268.6-35", Feb. 10, 2010, Publisher: German Patent Office, Published in: DE.
Japanese Office Action, dated Jul. 2, 2012 of Japanese Patent Application No. 2010-128582.
"Related Japanese Patent Application No. 2010-128582 Office Action", May 21, 2013, Publisher: JPO Published in: JP.

* cited by examiner

*Primary Examiner* — Paresh Patel

(74) *Attorney, Agent, or Firm* — Kaplan Breyer Schwarz & Ottesen, LLP

(57) ABSTRACT

A device for compensating magnetic fields, comprising a single magneto resistive sensor to which at least two parallel measuring amplifier loops are connected in series, one being an analogue broadband controller loop and the other being a digital broadband controller loop.

8 Claims, 4 Drawing Sheets

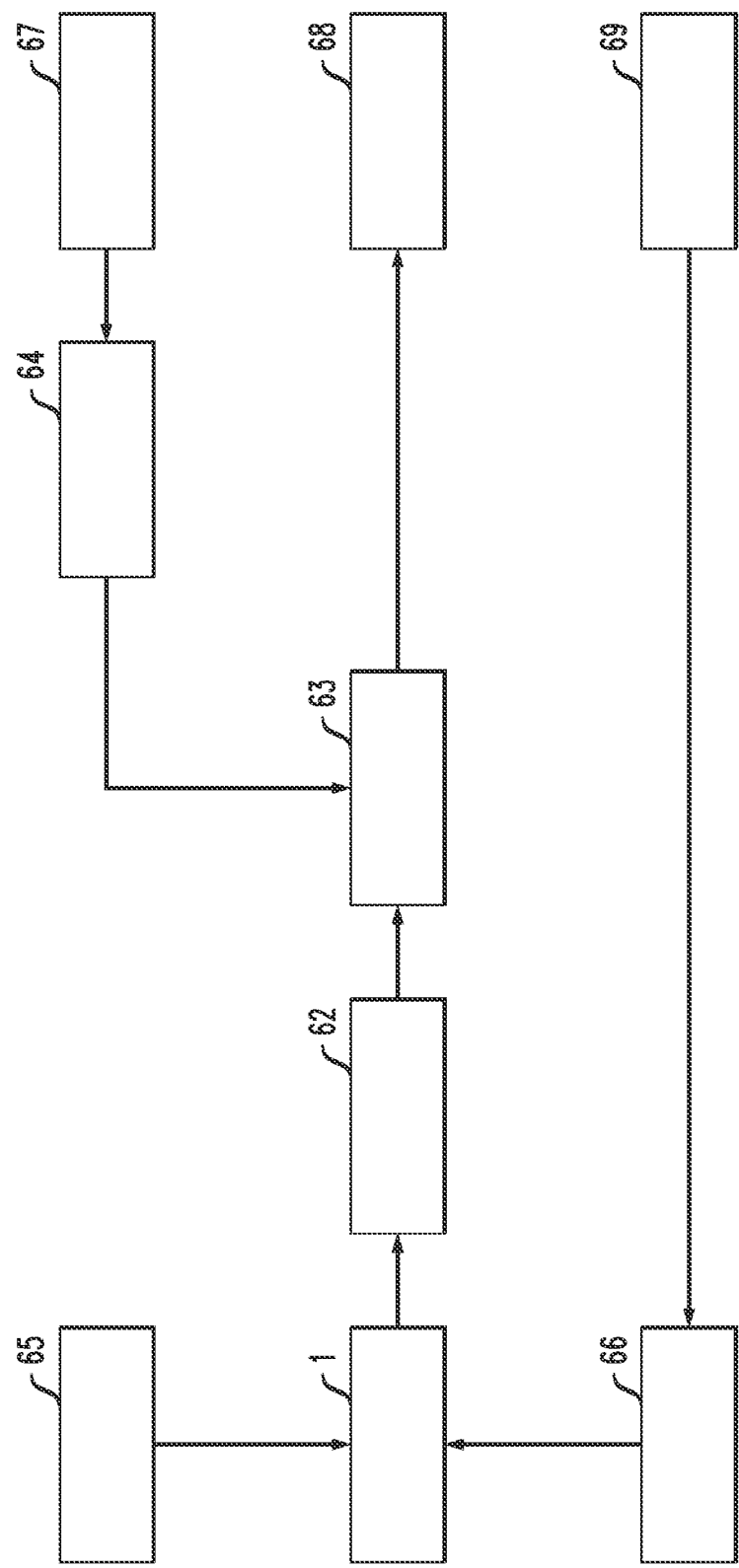

MAGNETIC FIELD COMPENSATION

CROSS-REFERENCE TO RELATED APPLICATIONS

German patent application DE 10 2009 024 268.6, filed Jun. 5, 2009, is incorporated herein by reference.

FIELD OF THE INVENTION

The invention relates to a device for magnetic field compensation, particularly to a magnetic field compensation device having a magneto resistive sensor.

BACKGROUND OF THE INVENTION

Devices for compensating magnetic fields are known. Such devices generally use a feedback control loop, wherein an interference field amplitude is measured by one or more sensors. Having been processed by means of a controlling device, the measured signal is passed as a control signal to Helmholtz coils, the locations of which minimize the interference field amplitude at the spot of the sensor by emitting a magnetic compensation field.

The magnetic field to be compensated may be the terrestrial magnetic field, or may be generated by other devices in the surroundings.

Feedback systems working only digitally may also be used besides feedback systems working only analogically. In order to avoid the disadvantages of such systems, hybrid systems were also developed.

Thus, the applicant's patent EP 1 873 543 A1 describes such a hybrid system for compensating magnetic fields. With this system for measuring the magnetic field, a combination sensor is used, which has coil sensing elements as well as flux gate sensors. The signals of the coil sensing elements are used in this connection for the analogue part of the controlling, the signals of the flux gate sensor for the digital part.

With coil sensing elements, the voltage induced by an external magnetic field in a coil is measured.

There are biaxial and triaxial flux gate sensors. Such sensors may measure magnetic fields perpendicular to a plane, or in all three directions in space. In doing so, three coils each are on two ferromagnetic cores. A triangle generator generates a current flowing through the excitation coils. A magnetic field is created in the ferromagnetic cores by this current. The change of the magnetic flux induces voltages in the so-called pick-up coils. If there is no external field, the difference of the voltages of the pick-up coils is zero. If an external field is created, a difference voltage is generated.

Such hybrid systems with an analogue and a digital control loop have the disadvantage that coil sensing elements as well as flux gate sensors have to be placed in one housing. In doing so, the physical proximity of the flux gate sensors to the coil sensing elements causes crosstalk of the chopper frequency to the coils, and therewith to undesired frequency components in the coil signal. In this context, the chopper frequency can be conceived of as the frequency with which the excitation coils of the flux gate sensor are operated. Therefore, the individual sensors have to be accurately arranged inside the housing, in order to keep this crosstalk small. Nevertheless, a structural shape of approximately 2 cm×2 cm×2 cm and a weight of 300 g can hardly be matched.

SUMMARY OF THE INVENTION

Therefore, it is the object of the invention to provide a sensor to be used in a compensating magnetic field device, the dimension thereof of the sensor being considerably smaller than in the case of conventional sensors.

Accordingly, a device for compensating magnetic fields is provided, which device comprises a magnetic field sensor, and a measuring amplifier for processing the measurement signal provided by the sensor. With this in mind, the magnetic field sensor is formed as a single magneto resistive sensor, to which at least two measuring amplifier loops are assigned, i.e. circuits for amplifying the measured signals so that these signals may be input to force amplifiers for exciting the compensation coils.

The operating mode of a magneto resistive sensor is based on magneto resistive effects. In case of these effects, by applying an external magnetic field, the electrical resistance of a material varies proportionally to the amplitude of the field. Particularly, the anisotropic magneto resistive effect (AMR effect), the "gigantic" magneto resistive effect (GMR effect), the CMR effect, the TMR effect, and the planar Hall effect are among the magneto resistive effects. With this in mind, it is distinguished between magneto resistive effects in non-magnetic material (Hall effect), in magnetic material (e.g. AMR effect), and in hybrid material consisting of non-magnetic and magnetic materials (e.g. GMR effect, CMR effect).

For clarity reasons, it should be pointed out that the usual Hall effect is not a magneto resistive effect, in contrast to the planar Hall effect.

The magneto resistive sensor is a triaxial sensor in one preferred embodiment of the invention.

Sensor signals from DC to 170 kHz, or even more, may be provided by such a device, by means of adding a low-noise electronics assembly.

One of the two measuring amplifiers is an analogue broadband controller, and the other one is a digital broadband controller. An analogue digital converter is arranged before the digital broadband controller. An analogue digital converter is arranged after the digital broadband controller. Here, the term "broadband" is to be understood in the sense of a large frequency spectrum, or a "broad" frequency band, in which the signals are present, and may be processed.

According to the invention, both measuring amplifier loops may be operated in parallel. Alternatively, the magnetic field sensor may be switched between the two measuring amplifier loops so that only the digital or the analogue measuring amplifier loop is used at any given time. In a preferred embodiment, the digital measuring amplifier comprises a plurality of parallel controllers for different frequency regions. By this means, the measuring signal of the magnetic field sensor is fed to different controllers, depending on its frequency components.

In a further embodiment, a low-pass filter for a frequency range from 0 to 1 kHz is connected in series to the digital broadband controller, and a high-pass filter for a frequency range from 1 kHz to at least 170 kHz is connected in series to the analogue broadband controller.

The frequency above which the measuring signal provided by the magnetic field sensor is not anymore input to the digital, but only to the analogue broadband controller, may also be in the order of magnitude of 20 Hz so that a low-pass filter for frequencies below 20 Hz is connected in series to the digital broadband controller, and a high-pass filter for frequencies above 20 Hz to the analogue broadband controller.

In a further embodiment of the invention, a selectable high-pass filter is connected in series to one of the two measuring amplifier loops so that the frequency above which the measuring signal provided by the magnetic field sensor is not anymore inputted to the digital, but only to the analogue broadband controller, may be manually set.

The magnetic field sensor is arranged inside Helmholtz coils for magnetic field compensation. In doing so, a pair of Helmholtz coils is each provided for each of the three directions in space. The output signals of the measuring amplifier loops are passed as control signals to the Helmholtz coils so that the magnetic field measured at the place of the magnetic field sensor is compensated.

One single coil per direction in space may be used instead of Helmholtz coils.

The magnetic field sensor according to the invention, including its at least two measuring amplifier loops, may be provided in a comparable compact structural shape. A single layer circuit board having a size of approximately 20 mm×4 mm×5 mm may be provided for one axis. Also in a triaxial embodiment, the magnetic field sensor according to the invention becomes significantly smaller, and lighter in weight than comparable sensor arrangements for compensating magnetic fields.

BRIEF DESCRIPTION OF THE DRAWINGS

FIG. 6 shows a block diagram of a measuring arrangement having a magneto resistive sensor.

DETAILED DESCRIPTION OF THE INVENTION

Figure 1:
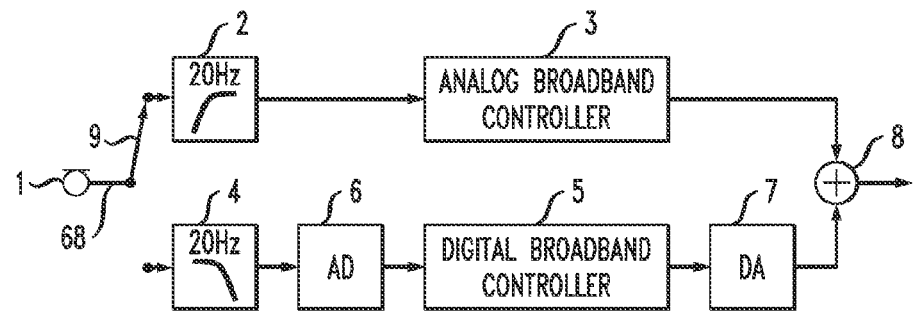
FIG. 1 shows an embodiment of a magnetic field measuring arrangement, with which an analogue broadband controller is connected in parallel to a digital broadband controller.

In the following, the invention is described in more detail referring to the attached figures, by means of exemplary embodiments, wherein same reference signs refer to the same components.

In a block diagram, FIG. 6 shows a measuring arrangement having a magneto resistive sensor. A magneto resistive sensor 1 in form of a chip is supplied with a reference voltage of 5V, by means of a voltage supply source 65. A reset switching circuit 66 allows a powering up of sensor 1, as well as an external reset through a flip coil, as is known in the art, being activated for demagnetizing the magneto resistive sensor chip, due to a reset signal 69. The output signal of sensor 1 is applied to an instrumentation amplifier 62 which amplifies the output signal. The amplification factor typically is about 200. The output signal of instrumentation amplifier 62 is applied to a summing amplifier 63 having a low-pass filter. The amplification factor of the summing amplifier 63 typically is about 36. The output signal 68 of summing amplifier 63, and therewith of the measuring arrangement, is digital and typically has a frequency of 120 kHz. The level of the output signal typically is at 140 mV per µT of the measured magnetic field. Each measuring arrangement according to FIG. 6 is provided for each of the three directions in space.

FIG. 1 shows a hybrid magnetic field measuring arrangement having one single magnetic field sensor 1, in which the output signal 68 of the measuring arrangement is fed into two measuring amplifier branches or loops arranged in parallel. The magnetic field sensor is switchable between the two measuring amplifier loops, via switch 9. Each of these measuring amplifier loops comprises one, two, or three amplifier channels, depending on the number of sensor axes, i.e. the particular signal has one or more components. The upper amplifier branch in FIG. 1 comprises an analogue broadband controller 3 with a high-pass filter 2 connected in series. The lower measuring amplifier branch or loop in FIG. 1 provides a low-pass filter 4, output signal thereof is fed in an analogue-digital (AD)-converter in series to a digital broadband controller 5. The digital output signal of the broadband controller 5 is converted into an analogue signal by a DA converter 7.

The output signals of the two measuring amplifier branches arranged in parallel are summed by an adder 8, and fed in a Helmholtz coil arrangement H having pairs of Helmholtz coils H1, H2, H3 (shown in FIG. 5) for forming a magnetic field compensation arrangement. A single coil may also be used per axis, instead of pairs of Helmholtz coils. The analogue and digital measuring amplifier branches are combined by measuring amplifier M, shown in FIG. 5.

The components of the output signal of the magnetic field measuring arrangement may be used for compensating magnetic fields, by using the signal components for controlling the particular current in the Helmholtz coils H1, H2, H3, or the single coils. These coils surround the place of or location of measurement, and therefore the magnetic field sensor 1. A feedback controlling concept is used, with which the interference field amplitude of the local magnetic field is measured by the sensor 1. Depending on the size of this interference field amplitude, accordingly controlled signal components are fed in the Helmholtz coils, or in the single coils so that the interference field amplitude at the place of measurement is minimized.

Analogue controllers and digital controllers have their particular advantages, and disadvantages. Analogue controllers cope with larger bandwidths, whereas digital controllers show a higher flexibility concerning control characteristics, with the possibility to use an alternative control program. Due to the analogue part of the magnetic field measuring arrangement, the disadvantage of solely digital systems is avoided. Hereto belongs that these systems not only need to carry out an AD conversion of the sensor signals, but also need to convert the output signals back into analogue signals.

Caused by this AD-DA conversion, due to scanning the signals, a phase loss results, which limits the bandwidth of the control in convenient controlling systems. Currently available digital systems achieve bandwidths of 1 kHz, maximally.

The combination of an analogue with a digital measuring amplifier branch avoids this disadvantage. In doing so, the output signal of magnetic field sensor 1 is split into its frequency parts. In the embodiment shown in FIG. 1, frequencies above 20 Hz are fed in the analogue broadband controller 3 by means of high-pass filter 2, and frequencies below 20 Hz are fed in the digital measuring branch including low-pass filter 4, converters 6, 7, and digital controller 5. The limit frequency may be chosen at a different frequency, for optimizing the efficiency factor of the two measuring amplifier branches arranged in parallel, for example.

Figure 2:
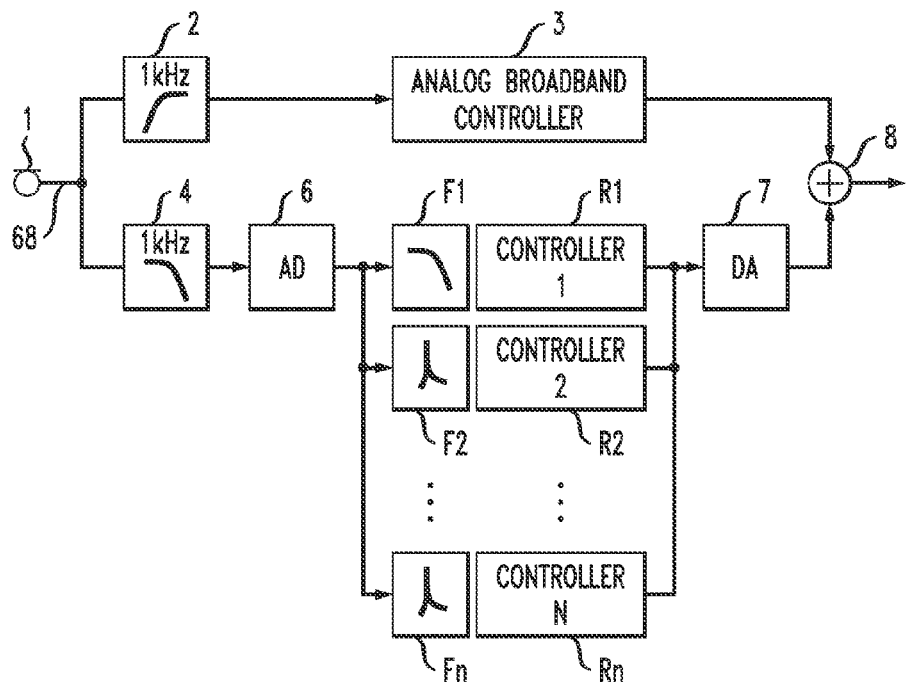
FIG. 2 shows an embodiment of a magnetic field measuring arrangement, with which an analogue broadband controller is connected in parallel to a digital broadband controller arrangement having several single frequency control loops.

FIG. 2 shows a further embodiment of a hybrid magnetic field measuring arrangement. Here too, the output signal 68 of the magneto resistive magnetic field sensor 1 is fed in two measuring amplifier branches arranged in parallel, whose upper branch, as in FIG. 1, again comprises an analogue broadband controller 3 with a high-pass filter 2 connected in series. In the lower branch, there is a parallel connection of several controllers R1, R2, ..., Rn, each of which includes a respective filter F1, F2, ..., Fn in series. The output signals of the controllers R1, R2, ..., Rn are summed, and converted into analogue signals by the DA converter 7, and fed in the adder 8.

Preferably, the filters F1, F2, ..., Fn are adjusted as follows:

F1: Low-pass filter 20 Hz
F2: 16, 67 Hz band-pass filter
F3: 50 Hz (or 60 Hz respectively) band-pass filter, according to local supply frequency
F4-Fn: Integer factor of the supply frequency, therefore 2*50 Hz/2*60 Hz, 3*50 Hz/3*60 Hz etc. as respective band-pass filter The split of the output signal 68 of sensor 1 by means of low-pass filter 4, and high-pass filter 2 is selected such that for both ranges, i.e. for the digital, low-frequency range as well as for the analogue, high-frequency range, the respectively optimal efficiency factor is achieved. Typically, these frequency ranges are from 0-2 kHz, 2 kHz-170 kHz, or from 0-4 kHz, 4 kHz-170 kHz, or more.

The output signal of the magnetic field measuring arrangement is used for compensating magnetic fields, as described.

Figure 3:
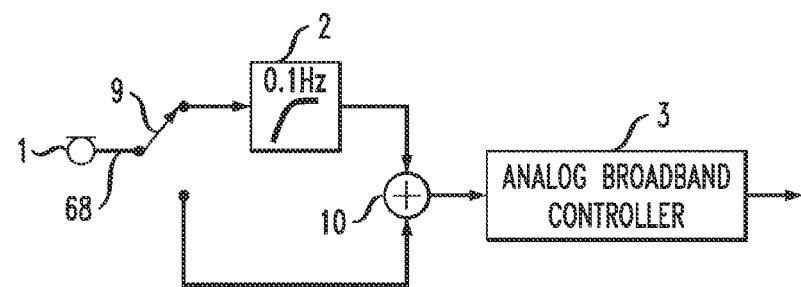
FIG. 3 shows an embodiment of a magnetic field measuring arrangement, with which a broadband controller comprises a selectable high-pass filter.

FIG. 3 shows a further embodiment of a magnetic field measuring arrangement, namely the analogue branch according to FIG. 1. The high-pass filter 2 connected in series to the analogue broadband controller 3 may be bridged by means of flipping a switch 9 so that the output signal 68 of the magneto resistive magnetic field sensor 1 reaches the analogue broadband controller 3 with its entire bandwidth without having been filtered. The filtered and the non-filtered output signal 68 of the magnetic field sensor 1 are summed by an adder 10.

The high-pass filter 2 connected in series conduces a band limitation of output signal 68 of sensor 1. Preferably, the filter frequency of the high-pass filter 2 is about 0.1 Hz, with this embodiment. The high-pass filter 2 is used, if a DC compensation is required. If this is not the case, the high-pass filter 2 is bridged by manually flipping the switch 9. Alternatively, the switch 9 may also be operated by means of software.

Here also, the components of the output signal of the magnetic field measuring arrangement are used for compensating magnetic fields.

Figure 4:
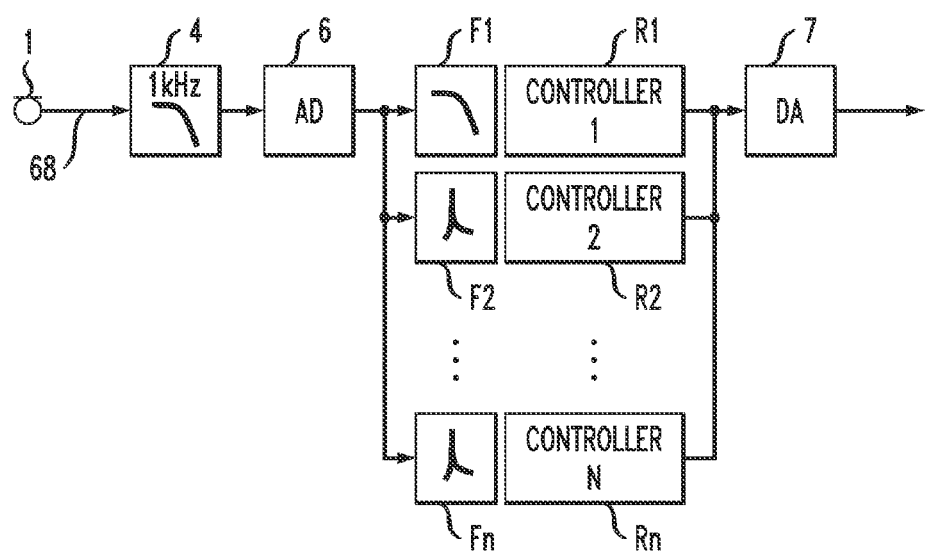
FIG. 4 shows an embodiment of a magnetic field measuring arrangement having a digital controller arrangement, and a fragmentation in single controllers for single frequencies.

FIG. 4 shows an embodiment of a digital magnetic field measuring arrangement principally corresponding to the lower measuring amplifier branch in FIG. 2. The arrangement comprises a low-pass filter 4, whose output signal is converted into a digital signal by an AD converter, which signal is fed in the single controllers R1, R2, ..., Rn arranged in parallel, with the filters F1, F2, ..., Fn connected in series. The filter frequency of the low-pass filter 4 preferably is from 1-5 kHz. The filters F1, F2, ..., Fn split the input signal between the controllers R1, R2, ..., Rn, depending on single frequencies. The frequencies are split between the filters F1, F2, ..., Fn, in the already described manner. The output signals of the controllers R1, R2, ..., Rn are converted into analogue signals by a DA converter in order to be used for compensating magnetic fields.

Figure 5:
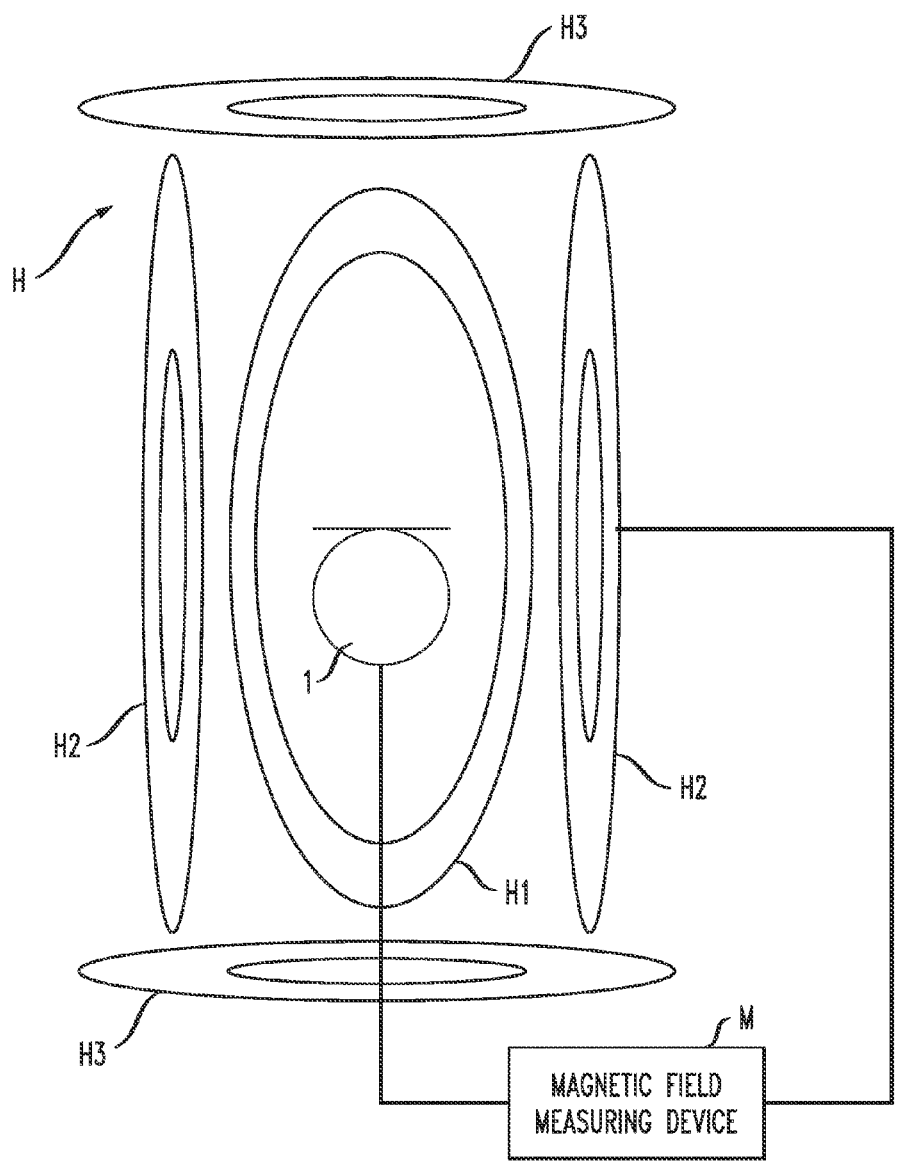
FIG. 5 shows an arrangement for compensating magnetic fields.

FIG. 5 shows the magneto resistive magnetic field sensor 1 in a magnetic field compensation arrangement H. The latter comprises one to three pairs of Helmholtz coils H1, H2, H3. Each pair of Helmholtz coils generates a magnetic field pointing in one direction of space. The magneto resistive magnetic field sensor 1 is arranged in the central area between the pairs of Helmholtz coils H1, H2, H3. The three components of the measuring signals 68 of the sensor 1 are passed to a magnetic field measuring device M, as described with respect to FIGS. 1-4. The measuring signals are amplified and processed before being passed back to the magnetic field compensation device. In doing so, the respective components of the signals are used as control signals for the pairs of Helmholtz coils H1, H2, H3.

In an alternative embodiment, single coils per axis in space are used instead of the pairs of Helmholtz coils.

What is claimed is:

1. A device for compensating magnetic fields, comprising:
a magnetic field measuring arrangement having
   (i) a magnetic field sensor, and
   (ii) measuring amplifier means;
wherein the measuring amplifying means have at least two measuring amplifying loops connected in parallel, of which a first loop is configured as an analogue broadband controller and a second loop is configured as a digital broadband controller, which comprises multiple controllers for different frequency ranges, connected in parallel; and
wherein the magnetic field sensor is a single triaxial magneto resistive sensor and is allocated in series to both the first loop and the second loop.

2. The device for compensating magnetic fields according to claim 1, wherein the magnetic field sensor is switchable between said at least two measuring amplifier loops.

3. The device for compensating magnetic fields according to claim 1, wherein said digital broadband controller loop is connected in series with a low-pass filter having a range from 0 to 1 kHz, and said analogue broadband controller loop is connected in series with a high-pass filter from 1 kHz to at least 170 kHz.

4. The device for compensating magnetic fields according to claim 1, wherein said digital broadband controller loop including connected in series a low-pass filter for frequencies below 20 Hz, and said analogue broadband controller loop includes connected in series a high-pass filter for frequencies above 20 Hz.

5. The device for compensating magnetic fields according to claim 1, wherein a selectable high-pass filter is connected in series to one of the at least two measuring amplifier loops.

6. The device for compensating magnetic fields, according to claim 1, wherein the single magneto resistive sensor is surrounded by a Helmholtz coil arrangement.

7. The device for compensating magnetic fields according to claim 1, wherein the single magneto resistive sensor is surrounded by a single coil arrangement.

8. The device for compensating magnetic fields according to claim 1, wherein the magnetic field sensor is switchable between said at least two measuring amplifier loops.

* * * * *